US006512954B2

(12) United States Patent
Fox et al.

(10) Patent No.: US 6,512,954 B2
(45) Date of Patent: Jan. 28, 2003

(54) IMPLANTABLE DEVICE AND PROGRAMMER SYSTEM WHICH PERMITS MULTIPLE PROGRAMMERS

(75) Inventors: James K. Fox, Lake Jackson, TX (US); William B. Rottenberg, Lake Jackson, TX (US); Bryan J. Thome, Houston, TX (US)

(73) Assignee: Intermedics, Inc., Angleton, TX (US)

( * ) Notice: Subject to any disclaimer, the term of this patent is extended or adjusted under 35 U.S.C. 154(b) by 0 days.

(21) Appl. No.: 09/981,972

(22) Filed: Oct. 16, 2001

(65) Prior Publication Data

US 2002/0035384 A1 Mar. 21, 2002

Related U.S. Application Data

(62) Division of application No. 09/191,808, filed on Nov. 13, 1998, now Pat. No. 6,308,099.

(51) Int. Cl.[7] .............................................. A61N 1/362
(52) U.S. Cl. .......................................... 607/31; 607/59
(58) Field of Search ............................ 607/30, 31, 59, 607/60

(56) References Cited

U.S. PATENT DOCUMENTS

| | | |
|---|---|---|
| 4,245,641 A | 1/1981 | Mann et al. |
| 4,365,633 A | 12/1982 | Loughman et al. |
| 4,401,120 A | 8/1983 | Hartlaub et al. |
| 4,432,360 A | 2/1984 | Mumford et al. |
| 4,550,370 A | 10/1985 | Baker |
| 4,571,589 A | 2/1986 | Slocum et al. |
| 5,456,692 A | 10/1995 | Smith, Jr. et al. |
| 5,620,472 A | 4/1997 | Rahbari |
| 5,690,690 A | 11/1997 | Nappholz et al. |
| 5,725,559 A | 3/1998 | Alt et al. |
| 5,843,138 A * | 12/1998 | Evers et al. .................. 607/30 |
| 5,891,178 A | 4/1999 | Mann et al. |

* cited by examiner

*Primary Examiner*—George R. Evanisko
(74) *Attorney, Agent, or Firm*—Schwegman, Lundberg, Woessner & Kluth, P.A.

(57) ABSTRACT

A multiprogrammer system for monitoring and optimizing implantable device performance. In one embodiment, the system includes at least two programming devices and an implantable device. Each of the programming devices may be used to perform inquiry and programming operations on the implantable device. In an inquiry operation, the programming device retrieves some or all of the configuration parameters from the implantable device. In a programming operation, the programming device provides one or more modified parameters to the implantable device. As part of the programming operation, the programming device is configured to verify that it is aware of the implantable device's current parameters before sending the modified parameters. In other words, the current programming device verifies that the implantable device's parameters have not been altered by another programming device since the current programming device's last interaction with the implantable device. If the parameters have been altered, the current programming device aborts the programming operation and notifies the operator. In alternate embodiments, the verification may be performed by the implantable device, i.e. the implantable device may verify that the programming device is aware of the current device parameters before the implantable device accepts the modified parameters.

11 Claims, 11 Drawing Sheets

IMPLANTABLE DEVICE AND PROGRAMMER SYSTEM WHICH PERMITS MULTIPLE PROGRAMMERS

This application is a Divisional of U.S. patent application Ser. No. 09/191,808 filed on Nov. 13, 1998, now issued as U.S. Pat. No. 6,308,099, the specification of which in hereby incorporated by reference.

BACKGROUND OF THE INVENTION

1. Field of the Invention

This invention relates generally to programming of implantable devices, and more particularly to a programming system which addresses the dangers raised by the presence of multiple programming devices.

2. Description of the Related Art

Implantable devices have become a standard method of treating various medical conditions, many of which relate to the heart. Examples of implantable devices include pacemakers, defibrillators, nerve stimulators, drug delivery devices, and implanted personal identification chips. Many types of implantable devices are available with high capacity memories for storing data and various programmable configuration parameters. In the case of medical devices, the data to be stored may include physiological data such as the electrogram (electrical waveform of the heart detected at the electrodes), instantaneous heart rate, blood pressure, volume pumped, body temperature, etc. Configuration parameters that are stored may include modes of operation, amplifier sensitivity, filter bandwidth, adaptation algorithms, output voltages, currents and pulse widths, blanking periods, various pacing rates, circadian response patterns, lead characteristics, delay intervals, detection thresholds, safety margins, logging criteria, and error messages. As implantable devices increase in sophistication, the number of configuration parameters is also expected to increase.

Referring now to FIG. 1, a human torso 102 is shown having an implantable device 106 coupled to a heart 104. When a wand 108 from an external programming device 110 is placed in proximity to implantable device 106, the programming device 110 can establish two-way communication with implantable device 106 to retrieve data and to provide new configuration parameters. Often the device 106 collects data over a period of hours or days. In the case of a pacemaker, the data may represent measured physiological signals such as cardiac voltages (EKG signals), blood temperatures, oxygen levels, sugar levels, and other physical parameters.

Illustratively, the programming device 110 comprises an implantable device programmer and data analyzer that is used by a physician. The programmer/analyzer operates to download information stored in implantable device 106 by transmitting signals which place the pacer in a mode for downloading, and thereafter detecting signals sent by the device. Then, under control of the physician or other medical professional, the programmer/analyzer operates to analyze and display the information in a format which allows the physician to diagnose any problems. After performing an analysis, the physician may instruct the programmer/analyzer to adjust operating parameters for a different mode of operation, sensitivity setting, or other parameter value, to tailor the behavior of the device to the patient and thereby optimize the patient's quality of life. If this is the case, the programmer/analyzer 10 provides new operating parameters to the implantable device 106.

Implant manufacturers have long been aware of a danger known as the "multiple programmer" problem which can result in an implantable device having incorrect and perhaps even dangerous or harmful configuration parameters. The following scenario is presented to illustrate this problem.

A patient with an implantable device enters an examination room, and as part of a routine initial examination has a medical technician use a first programming device "A" to download data and configuration parameters from the implantable device. Depending on the amount of data and the baud rate of the device, the download time may range from 20 seconds to 20 minutes. In the absence of any gross abnormalities in the downloaded data, the patient is sent to another room for an exercise session to determine "rate modulated" settings, i.e. configuration parameters for adjusting the pacemaker pace rate in response to detecting patient exertion. In this room, a physician uses a second programming device "B" to download and adjust the configuration parameters in response to the results of the exercise session. Programming device "B" is used to reprogram the implantable device with the adjusted parameters. The patient then returns to the examination room, where a physician uses programming device "A" to adjust some of the configuration parameters in response to analysis of the downloaded data. Programming device "A" is then used to reprogram the implantable device with the adjusted parameters. It is important to note that programming device "A" is, at this point, operating with an obsolete version of the implant's configuration settings. This situation occurs whenever changes are made to the implantable device's configuration parameters by a second programming device "B" between the download and reprogramming operations of the first programming device "A".

The configuration parameters of an implantable device such as a pacemaker can individually be set to typical values within a normal operating range, but the programming device must still check for incompatible parameter settings to avoid dangerous combinations of parameter values. For example, programming an inappropriately long refractory period in conjunction with a short pacing cycle may lead to unpredictable pacing behavior. If a programming device with an obsolete version of the implant device's configuration settings reprograms only a few parameters, any safeguards that the programming device implements to avoid incompatible parameter settings could be unintentionally circumvented.

One programmer safeguard that has been employed is to have programming device "A" reprogram the implantable device with a complete set of configuration parameters rather than just the parameters which have been adjusted. Although this successfully prevents incompatible configuration settings, the previous adjustments are completely undone without any indication to the physician. Further, the reprogramming time is unnecessarily increased beyond what may be strictly necessary.

The solution commonly employed by implant manufacturers has been simply to issue warnings regarding the danger of using multiple programming devices. A more effective and inexpensive solution to the multiple programming device problem is desirable.

SUMMARY OF THE INVENTION

Accordingly, there is provided herein a multiprogrammer system for monitoring and optimizing implantable device performance. In one embodiment, the system includes at least two programming devices and an implantable device. Each of the programming devices may be used to perform inquiry and programming operations on the implantable device. In an inquiry operation, the programming device retrieves some or all of the configuration parameters from the implantable device. In a programming operation, the programming device provides one or more modified parameters to the implantable device. As part of the programming operation, the programming device is configured to verify that it is aware of the implantable device's current parameters before sending the modified parameters. In other words, the current programming device verifies that the implantable device's parameters have not been altered by another programming device since the current programming device's last interaction with the implantable device. If the parameters have been altered, the current programming device aborts the programming operation and notifies the operator. In alternate embodiments, the verification may be performed by the implantable device, i.e. the implantable device may verify that the programming device is aware of the current device parameters before the implantable device accepts the modified parameters.

As part of the multiprogrammer system provided herein, there is disclosed a programming device embodiment, an implantable device embodiment, and various methods for verifying that the programming device has been provided with a current version of the implantable device's configuration parameters. The programming device preferably comprises a user interface, a memory, a communications circuit, and a microprocessor. The communications circuit generally includes a communication coil, receive sensor, modulator, and demodulator, and is configurable to send and receive configuration parameters to and from the implantable device. The microprocessor couples to the user interface, the memory, and the communications circuit, and it operates under control of the user interface to retrieve configuration parameters from the implantable device and to store the parameters in memory. The configuration parameters may be modified, and the modified parameters can be sent to the implantable device. In certain disclosed embodiments, the microprocessor uses one of the following methods to verify that the stored configuration parameters are "current" before sending the modified parameters, that is, the microprocessor verifies that the implantable device's parameters have not been altered since this programmable device last retrieved the implantable device's parameters.

The implantable device comprises a microprocessor coupled to a memory and a telemetry module. The memory stores configuration parameters, and the telemetry module transmits and receives external communications. The microprocessor performs some algorithm in a manner governed by the configuration parameters stored in the memory. In certain disclosed embodiments, the microprocessor uses one of the following methods to verify that an external programming device has received a current version of the configuration parameters before accepting modified configuration parameters from the programming device.

The disclosed methods for verifying that a programming device is aware of the implantable device's current configuration parameters include: (1) providing a programming device serial number to the implantable device as part of every inquiry operation; (2) allowing a programming operation only within a predetermined time interval after an inquiry operation; (3) storing the date and time of the most recent inquiry operation; (4) storing the date and time of the most recent programming operation; and (5) retrieving the implantable device's current parameters as part of every programming operation. For method (1), the implantable device or the programming device can be configured to compare the programming device's serial number with the serial number of the last programming device to retrieve the implantable device's configuration parameters. A match indicates that the programming device is aware of the implantable device's current parameter values.

For method (2), the implantable device or the programming device can determine if the downloaded version of the configuration parameters has "expired", that is, whether a predetermined amount of time has passed since the configuration parameters were last retrieved. For method (3), the implantable device or programming device can be configured to compare the date and time of the most recent inquiry stored in the programming device to that stored in the implantable device. A match indicates that the programming device is aware of the implantable device's current parameter values.

Similarly, for method (4), the implantable device or programming device can be configured to compare the date and time of the most recent programming operation stored in the programming device to that stored in the implantable device. Finally, for method (5), the programming device can be configured to retrieve the implantable device's configuration parameters immediately prior to a programming operation to verify that the programming device has a current version. These methods will be described in more detail further below.

BRIEF DESCRIPTION OF THE DRAWINGS

Other objects and advantages of the invention will become apparent upon reading the following detailed description and upon reference to the accompanying drawings in which.

Figure 1:
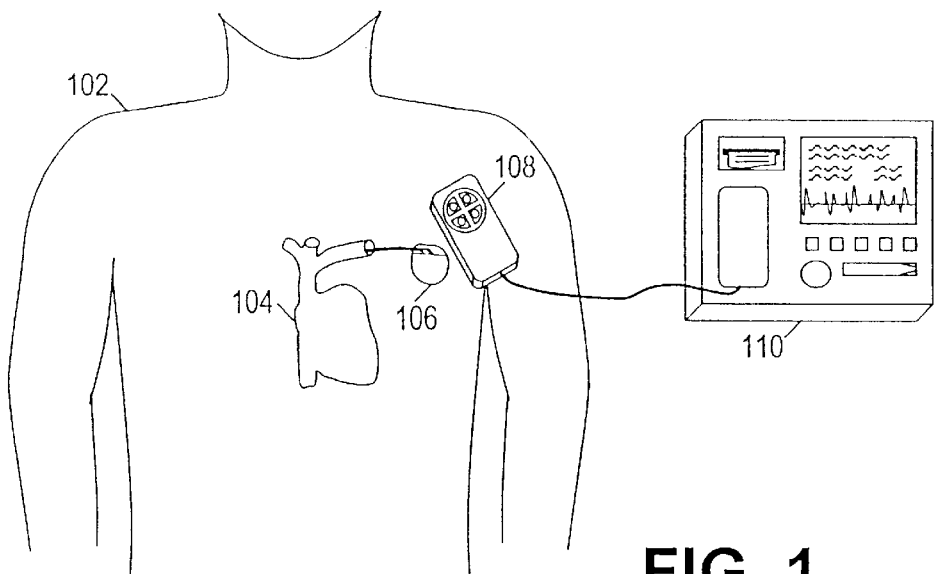
FIG. 1 shows an implantable medical device and a programming device.

While the invention is susceptible to various modifications and alternative forms, specific embodiments thereof are shown by way of examples in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description illustrates the principles of the present invention with respect to an implantable pacemaker ("pacer") and a programming device ("programmer"). The invention, however, is directed to a system for permitting multiple programming devices to interact with an implantable device. Thus, the invention applies to implantable cardioverter/defibrillators (ICD's), nerve stimulators, drug delivery devices, or any other implantable device which may have programmable configuration parameters set by a programming device.

Figure 2:
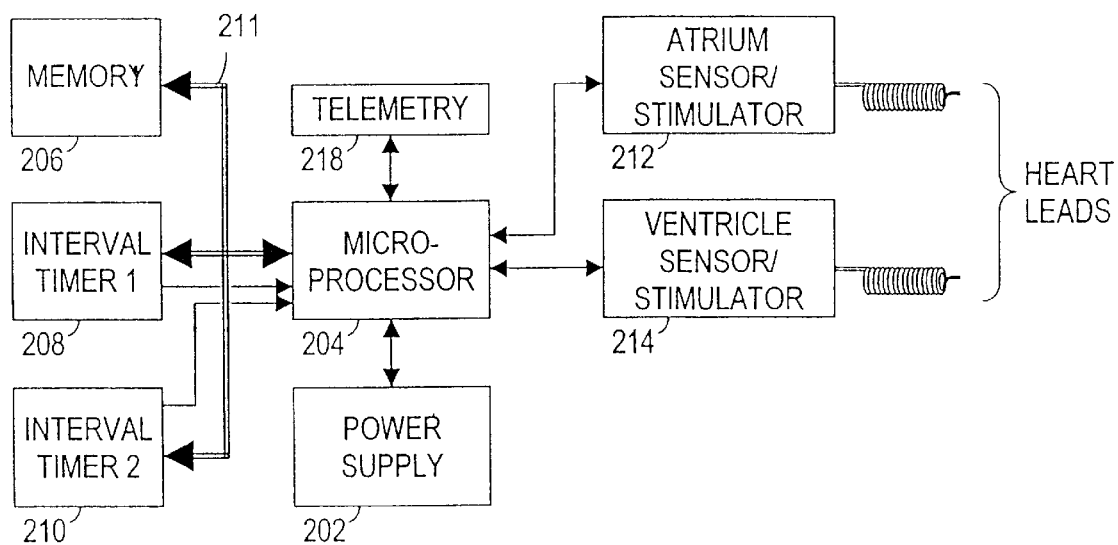
FIG. 2 is a block diagram of an implantable pacemaker.

Referring now to FIG. 2, an exemplary implantable device 106 (such as a pacemaker) preferably includes a power supply 202 coupled to a microprocessor 204. The power supply 202 provides power to all the devices shown in FIG. 2 through connections which are not specifically shown. In the exemplary embodiment, the microprocessor 204 couples to a memory 206, a first interval timer 208, and a second interval timer 210 via an I/O (input/output) bus 211. The microprocessor 204 also couples to control an atrium sensor/stimulator 212 and a ventricle sensor/stimulator 214, each of which may be coupled to the heart by flexible leads. Finally, microprocessor 204 couples to a telemetry module 218 to communicate with programming device 110.

The microprocessor 204 preferably is programmable and operates according to a program stored preferably in a nonvolatile memory such as a read-only memory (not specifically shown). The program is parameterized—i.e. one or more of the operations the microprocessor performs is alterable by setting a configuration parameter. For example, the microprocessor may be programmed to periodically trigger the atrium sensor/stimulator 212 to deliver a pulse to the heart 104. In this instance, one of the configuration parameters for this operation is the maximum trigger delay, that is, a value specifying the maximum time delay before the atrium stimulator is triggered. The maximum trigger delay, along with other configuration parameters, is provided to microprocessor 204 via telemetry module 218 and stored in memory 206. During pacemaker operation, the microprocessor 204 retrieves the maximum trigger delay from the memory 206 and uses it to set interval timer 210 after each triggering of the atrium sensor/stimulator. If the interval timer 208 expires, the microprocessor then triggers atrium sensor/stimulator 212.

Referring still to FIG. 2, the first interval timer 208 determines the delay between trigger signals applied to atrium stimulator 212 and ventricle stimulator 214. The second interval timer 210 measures the time since the last heartbeat sensed by the atrium sensor/stimulator 212 or ventricle sensor/stimulator 214. When either timer elapses, the elapsed timer asserts an interrupt signal to microprocessor 204 to notify the microprocessor 204 that the set amount of time has passed. Microprocessor 204 determines the source of the interrupt according to conventional techniques and takes the appropriate action. For example, if the maximum trigger delay (interval timer 210) has elapsed since the last heartbeat, the microprocessor 204 triggers atrium sensor/stimulator 212.

The microprocessor 204 also preferably monitors one or more physiological signals. In the pacemaker example, the microprocessor 204 detects cardiac voltage signals via atrium sensor 212 and/or ventricle sensor 214. The heart leads which provide electrical pulses to the heart may also be used to sense electrical signals created by the heart as it beats, and these signals are used by the microprocessor 204 to adjust the timing of the electrical pulses. When other sensors are coupled to the implantable device 106, the microprocessor can also monitor blood pressure, body temperature, oxygen levels, and other physiological parameters. The microprocessor 204 can also track its own performance, perhaps by logging the manner in which adaptation is performed on the parameters. The physiological signals and performance information can be logged in memory 206 for later retrieval by programming device 110. The memory 206 preferably is large enough to store data regarding several physiological signals that being are monitored over a period of several days. Memory 206 preferably is implemented as dynamic random access memory (DRAM) or other suitable memory type.

The atrium sensor/stimulator 212 is an interface circuit between microprocessor 204 and a heart lead coupled to an atrium of the heart. An interface circuit is necessary to allow the digital, low voltage microprocessor to control the high-energy pulses delivered to the heart, and additionally, to allow the microprocessor to monitor the analog electrical signals that are generated by the heart as it beats. Similarly, the ventricle sensor/stimulator 214 is an interface circuit between microprocessor 204 and a heart lead that couples to a ventricle of the heart. When atrium sensor/stimulator 212 receives a trigger signal from microprocessor 204, it generates a shaped electrical energy pulse to the atrium. Likewise, when ventricle sensor/stimulator 212 receives a trigger signal from microprocessor 204, it provides a shaped electrical energy pulse to the ventricle. If the microprocessor is using atrium sensor/stimulator 212 or ventricle sensor/stimulator 214 to measure cardiac voltage signals from the electrodes to monitor the performance of the heart, the microprocessor 204 stores the cardiac waveforms (or "electrograms") in memory for subsequent retrieval by a medical technician.

Telemetry module 218 may be designed to be activated by programming device 110 when wand 108 enters into proximity with pacer 106. For example, the telemetry module 218 may continually be checking for an activation signal that the wand 108 transmits. Activation of the telemetry module 218 causes the telemetry module 218 to establish bidirectional communication with wand 108 and to notify microprocessor 204 of an incoming communication. As the wand 108 transmits a message signal, the telemetry module demodulates the message signal and delivers the incoming message to the microprocessor 204. The microprocessor 204 decodes the incoming message and stores any received data or parameters. In addition, the microprocessor 204 responds to any received commands from the programming device 110. For example, one command might be an "inquiry", that is, a request for the microprocessor 204 to transfer configuration parameters from memory 206 to programming device 110. In this case, microprocessor 204 provides the configuration parameters from memory 206 to telemetry module 218 for transferal to programming device 110.

Figure 3:
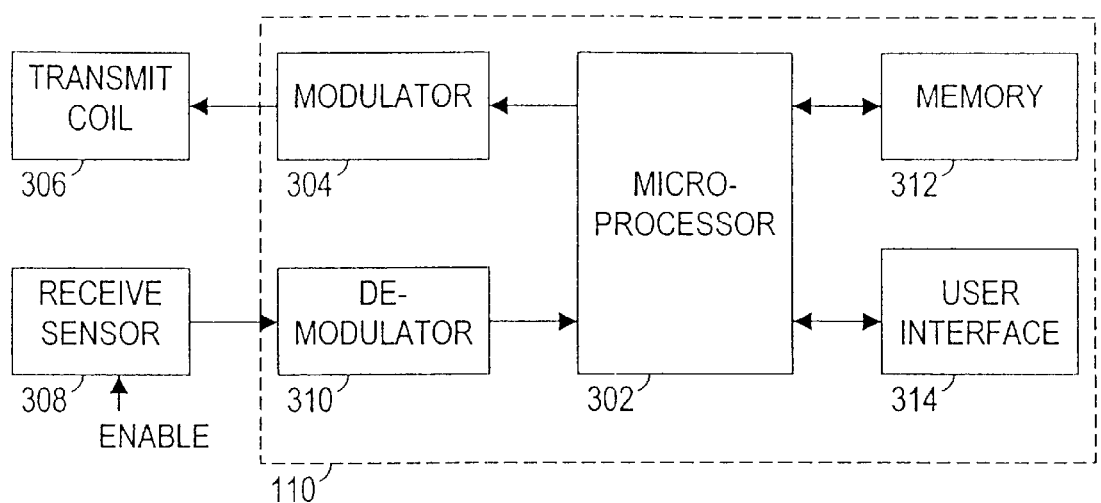
FIG. 3 is a block diagram of an exemplary embodiment of a programming device.

Referring now to FIG. 3, programming device 110 includes a microprocessor 302, a modulator 304 coupled to a transmit coil 306, a demodulator 310 coupled to a receive sensor 308, a memory 312, and a user interface 314. The microprocessor 302 responds to user input via the user interface 314 (which may comprise a graphic display and user input device such as a keypad) and initiates communications with pacer 106 (FIG. 2). For example, if a user requests a download of data from the pacer to programming device 110, microprocessor 302 formulates a command signal, and sends the signal to modulator 304. Modulator 304 converts the command signal into a modulated signal for driving transmit coil 306. The signal driving the transmit coil 306 produces a changing magnetic field which induces a current in a receive coil in the pacer. The pacer processes the induced current to reconstruct the information sent from the programming device, and formulates and sends a reply. The pacer can transmit signals to programming device 110 by various means including modulating a light signal or driving a transmit coil. Receive sensor 308 detects and amplifies the signal transmitted by the pacer to produce a detection signal. Demodulator 310 demodulates the detection signal and converts it into the data transmitted by the pacer 106. Demodulator 310 then provides the data to microprocessor 302 for eventual analysis and display via user interface 314. Memory 312 may be used to store data and configuration parameters downloaded from the pacer.

Figures 4, 5:
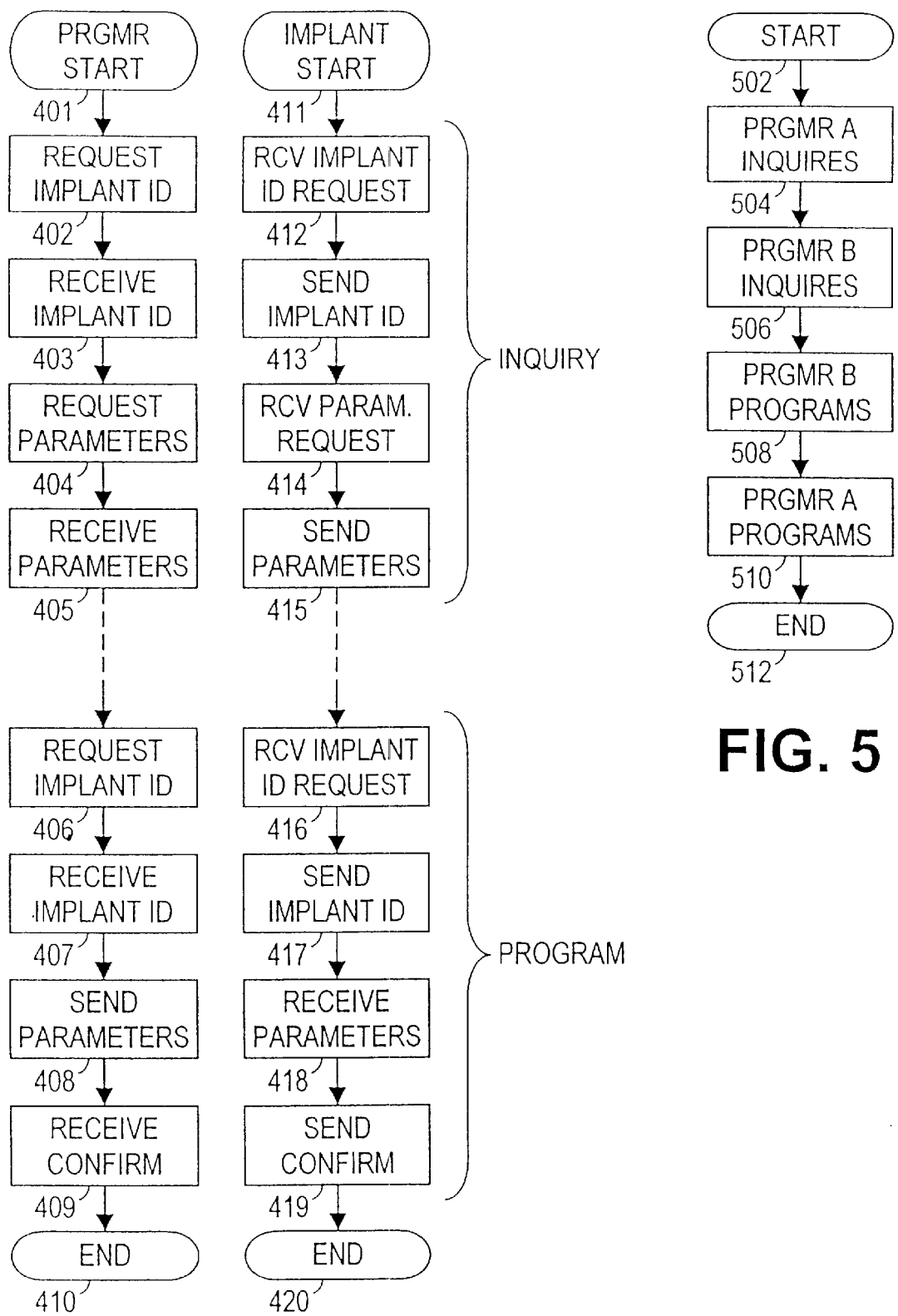
FIG. 4 is a flowchart depicting a method for performing inquiry and programming operations.
FIG. 5 is a flowchart illustrating the multiprogrammer problem.

Referring now to FIG. 4, a pair of flowcharts are provided to illustrate the operation of the processor 302 in the programming device 110 and the operation of the processor in 204 the implantable device 106 during the inquiry and programming operations. The programming device's processor 302 starts in step 401 and the implantable device's processor 204 starts in step 411. In step 402 the processor 302 initiates an inquiry operation by sending a command to the implantable device requesting the implantable device to transmit its model and serial number. In step 403 the processor 302 receives the model and serial number information and stores it for future identification of the implantable device. In step 404 the processor 302 sends a request to the implantable device for the implantable device to transmit one or more of its configuration parameters. The parameter request may be a partial request, in which only certain specified parameters are requested, or a full request, in which a download of all the configuration parameters is requested. In a typical initial inquiry operation, the parameter request is a full request. In step 405 the processor 302 receives the transmitted configuration parameters and stores them in memory for analysis and possible alteration by the user of the programming device 110. This may complete the inquiry operation, or as a further part of the inquiry operation the processor 302 may request and receive stored physiological data from the implantable device.

After a user examines the configuration parameters and analyzes any downloaded data, the user may wish to modify one or more of the configuration parameters and to perform a programming operation to reprogram the implantable device with the modified parameters. In step 406 the processor 302 initiates a programming operation by sending a command to the implantable device requesting the implantable device to transmit its model and serial number. In step 407 the processor 302 receives the model and serial number information and verifies that it matches with the stored identification information from step 403. The processor then in step 408 transmits the modified parameters. The programming device transmits a partial or complete parameter set to the implantable device. A partial parameter set is preferred for a faster programming operation, but a complete parameter set is preferred for added safety against incompatible configuration parameter settings. In step 409 the processor 302 receives confirmation from the implantable device that the transmitted parameters were successfully received. If confirmation is not received, in step 409, then the user is notified of a failure to reprogram the implantable device. The processor 302 completes the programming operation by entering into end state 410.

In step 412 processor 204 of the implantable device receives the model and serial number request command sent by the programming device in step 402. In step 413 the processor 204 responds by transmitting the model and serial number of the implantable device. In step 414 the processor 204 receives the configuration parameter request command from the programming device, and in step 415 the processor responds by transmitting the current configuration parameter values. Subsequently during a programming operation, the processor 204 receives another model and serial number request command in step 416, and responds in step 417 by transmitting the model and serial number of the implantable device. Then in step 418 the processor 204 receives modified parameter values from the programming device. After verifying that the parameters have been correctly received, the processor updates the configuration parameters with the new values and, in step 419, transmits a confirmation message to the programming device.

FIG. 5 illustrates how the use of multiple programming devices can introduce safety concerns when a second programming device interacts with an implantable device between the inquiry and programming operations of the first programming device. An implantable device begins in step 502. In step 504, an inquiry operation is performed by a first programming device "A". Subsequently, a second programming device "B" performs an inquiry operation on the implantable device in step 506, and a programming operation on the implantable device in step 508. The first programming device "A" is then used to program the implantable device in step 510, and at the end of this sequence in step 512, the implantable device may be left with an undesired set of configuration parameters. To avoid this, programming device "A" or the implantable device may be provided with a means for detecting if another programming device interacted with the implantable device between the inquiry and program operations of programming device "A".

Figure 6:
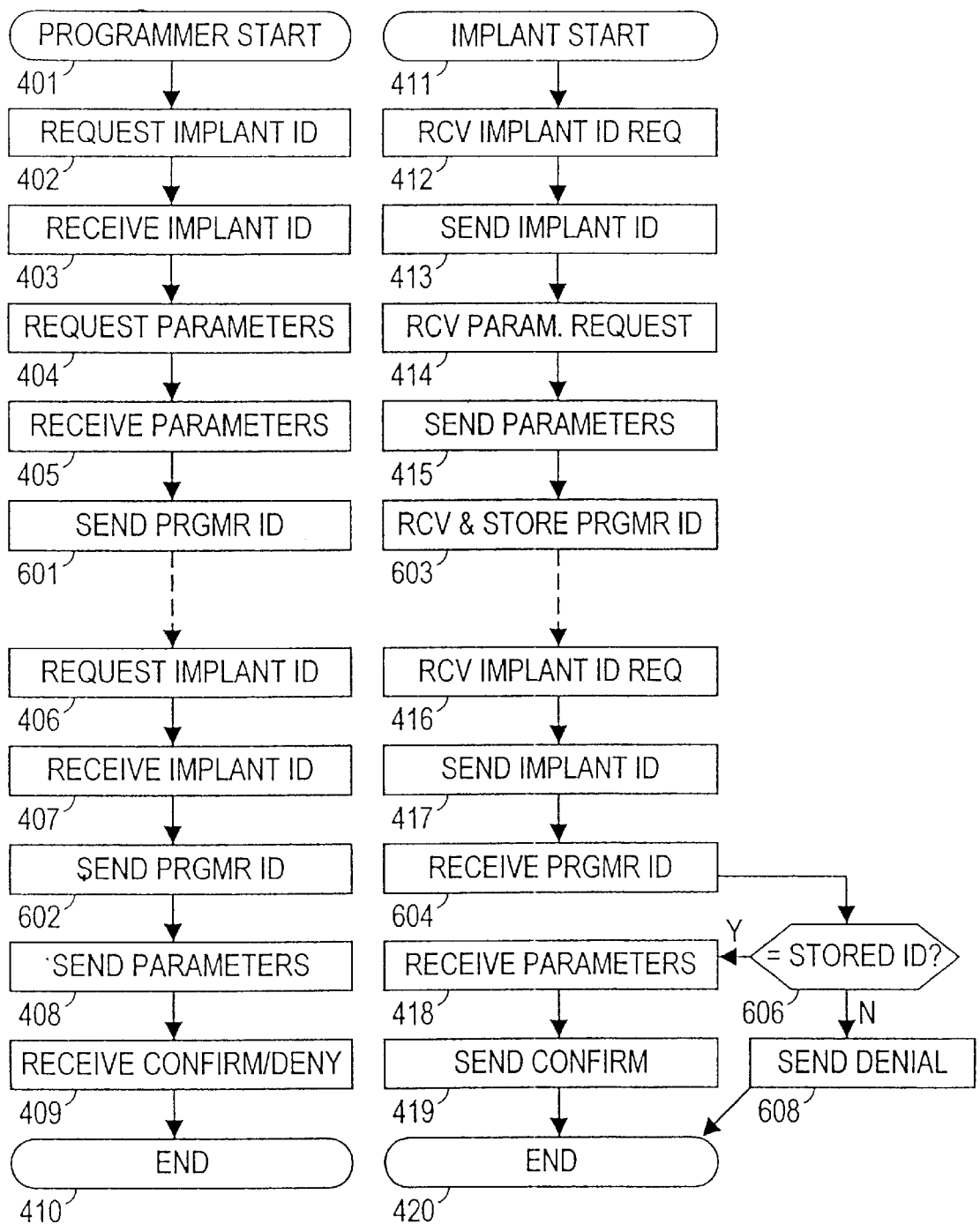
FIG. 6 is a flowchart depicting a first method for performing inquiry and programming operations in a multiprogrammer environment.

A first embodiment of a multiple programming device-implantable device system is shown in FIG. 6. The programming device's processor 302 proceeds through the inquiry operation steps 401–405 as outlined previously. After the processor 302 successfully receives all the requested parameters in step 405, in step 601 the processor 302 sends a programming device identification number to the implantable device for the implantable device to store. The programming device identification number preferably includes the model number and serial number of the programming device. In this system embodiment, the implantable device always has a record of the last programming device to successfully perform an inquiry or programming operation on it.

Subsequently, when the programming device is ready to transmit altered parameters to the implantable device, the processor 302 proceeds through steps 406, 407, and after verifying that the implant identification information matches, the processor transmits the programming device identification number in step 602 before transmitting the modified configuration parameters in step 408 and proceeding through steps 409 and 410.

The implantable device's processor 204 similarly proceeds through inquiry operation steps 411–415 as outlined previously. After the processor 204 transmits the requested parameters in step 415, it receives and stores the programming device identification information in step 603. Then when the programming device initiates a programming operation, the processor 204 performs steps 416, 417 before receiving the programming device's identification information in step 604. In step 606 the processor 204 compares the received identification information to the previously stored identification information from step 603. If they do not match, then in step 608 the processor 204 transmits a denial to the programming device and ends the programming operation in step 420. If the information matches, then the processor 204 performs steps 418–420 to accept and confirm the modified parameters.

This system embodiment provides that only the programming device which has most recently interacted successfully with the implantable device is allowed to program the implantable device. Referring back to FIG. 5, in step 510 this embodiment of programming device "A" would receive a denial from the implantable device when a programming operation is attempted. Programming device "A" would preferably inform the user of the denial and allow the user to initiate an inquiry operation to discover any alterations which may have been made to the configuration parameters.

Figure 7:
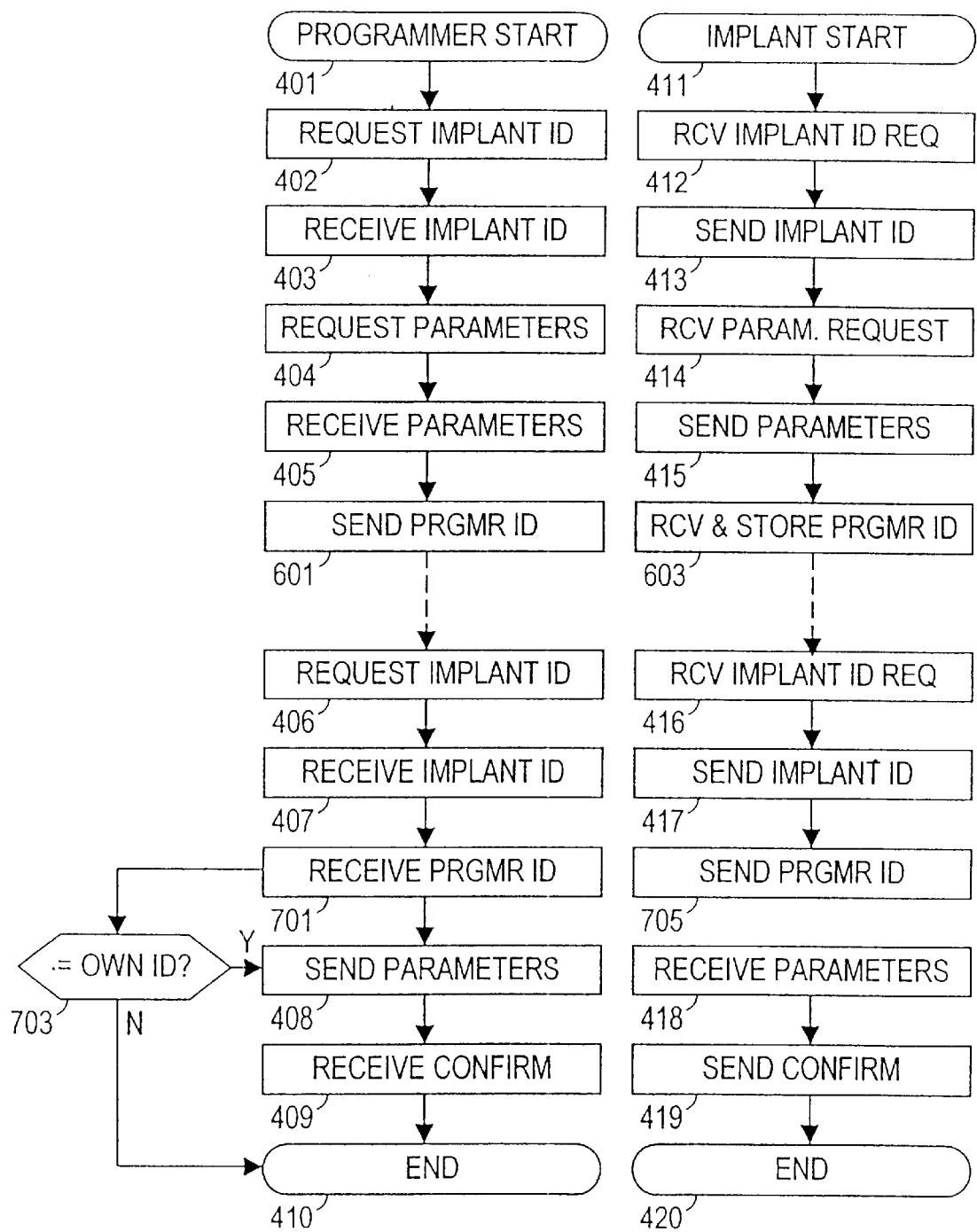
FIG. 7 is a flowchart depicting a second method for performing inquiry and programming operations in a multiprogrammer environment.

Another system embodiment is illustrated in FIG. 7. The inquiry operation of this embodiment matches that of the previous embodiment for both the programming device and the implantable device. After step 417 of the programming operation, the implantable device's processor 204 sends the programmer identification information to the programmer device in step 705. Then in step 418, the processor 204 receives any transmitted parameters and proceeds through steps 419, 420 as outlined. previously.

After step 407 of the programming operation the programming device's processor 302 receives in step 701 the identification information of the last programmer to interact with the implantable device. In step 703 the processor 302 verifies that the identification information matches the programming device's model and serial number. If they do not match, the processor 302 terminates the programming operation in step 410 and preferably notifies the user of the error. Otherwise, the processor proceeds through steps 408–410 of the programming operation to provide the modified parameters to the implantable device. This embodiment advantageously places fewer demands on the implantable device, thereby minimizing implementation cost.

Figure 8:
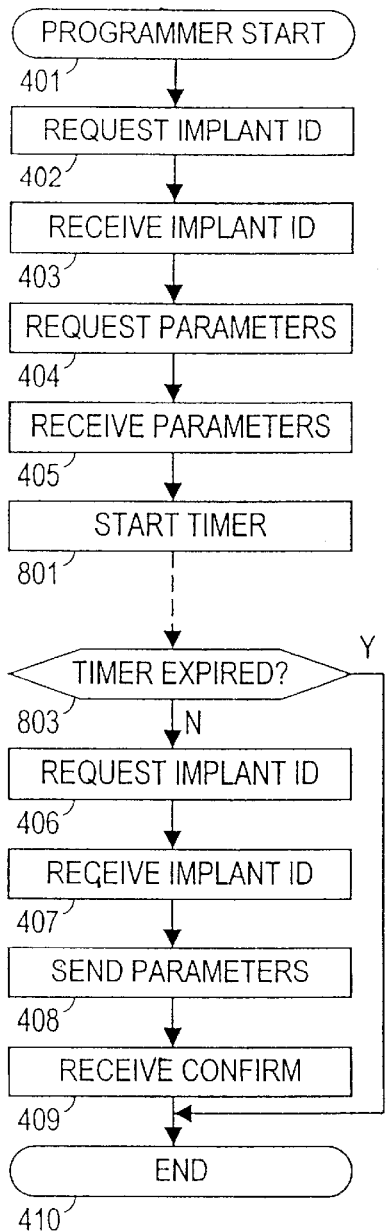
FIG. 8 is a flowchart depicting a third method for performing inquiry and programming operations in a multiprogrammer environment.
Figure 9:
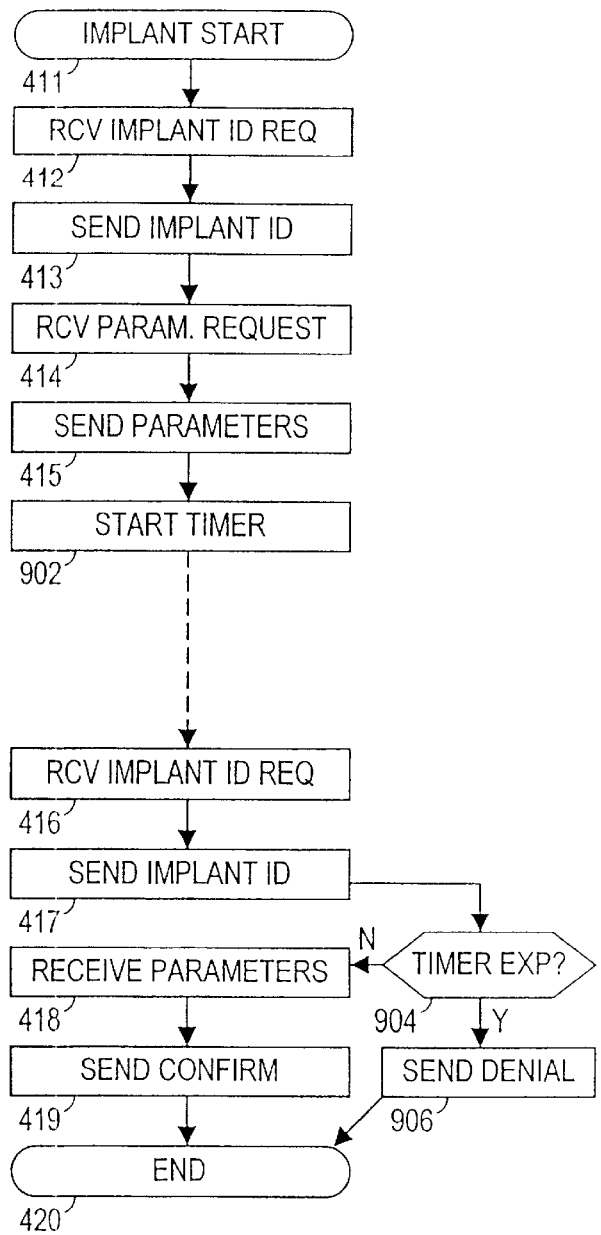
FIG. 9 is a flowchart depicting a fourth method for performing inquiry and programming operations in a multiprogrammer environment.

Another programming device embodiment is shown in FIG. 8. In this embodiment, after successfully receiving the configuration parameters in step 405, the programming device's processor 302 starts a timer in step 801. Subsequently, before initiating a transmission of altered parameters, the processor 302 checks for expiration of the timer in step 803. If too much time has elapsed, the processor 302 aborts the programming operation and preferably notifies the operator. Otherwise, the processor 302 continues with the programming operation in steps 406–410. An implantable device embodiment which operates similarly is shown in FIG. 9. After successfully completing transmission of requested parameters, the implantable device's processor 204 starts a timer in step 902. After a programming operation is initiated, the processor 204 checks for expiration of the timer in step 904. If too much time has elapsed, the processor 204 transmits a denial in step 906, and the programming device preferably notifies the operator of the failure of the programming operation. Otherwise, the processor 204 continues the programming operation in steps 418–420. In a variation on the embodiments of FIGS. 8 and 9, the timers may be restarted after successful completion of the programming operation. The timers in FIGS. 8 and 9 preferably run for a time period greater than 5 minutes and less than 60 minutes. A time period of between 10 and 20 minutes is contemplated.

Figure 10:
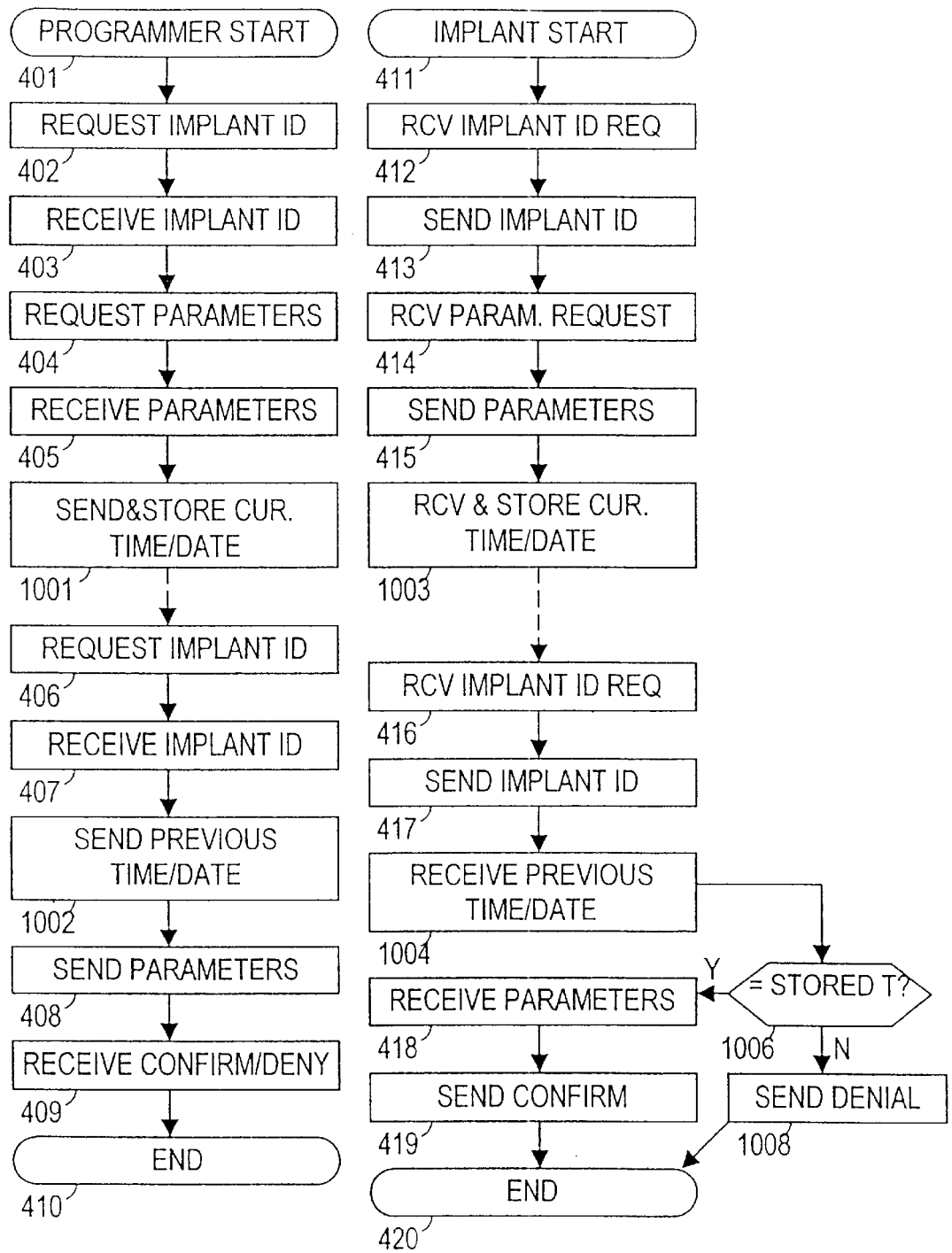
FIG. 10 is a flowchart depicting a fifth method for performing inquiry and programming operations in a multiprogrammer environment.
Figure 11:
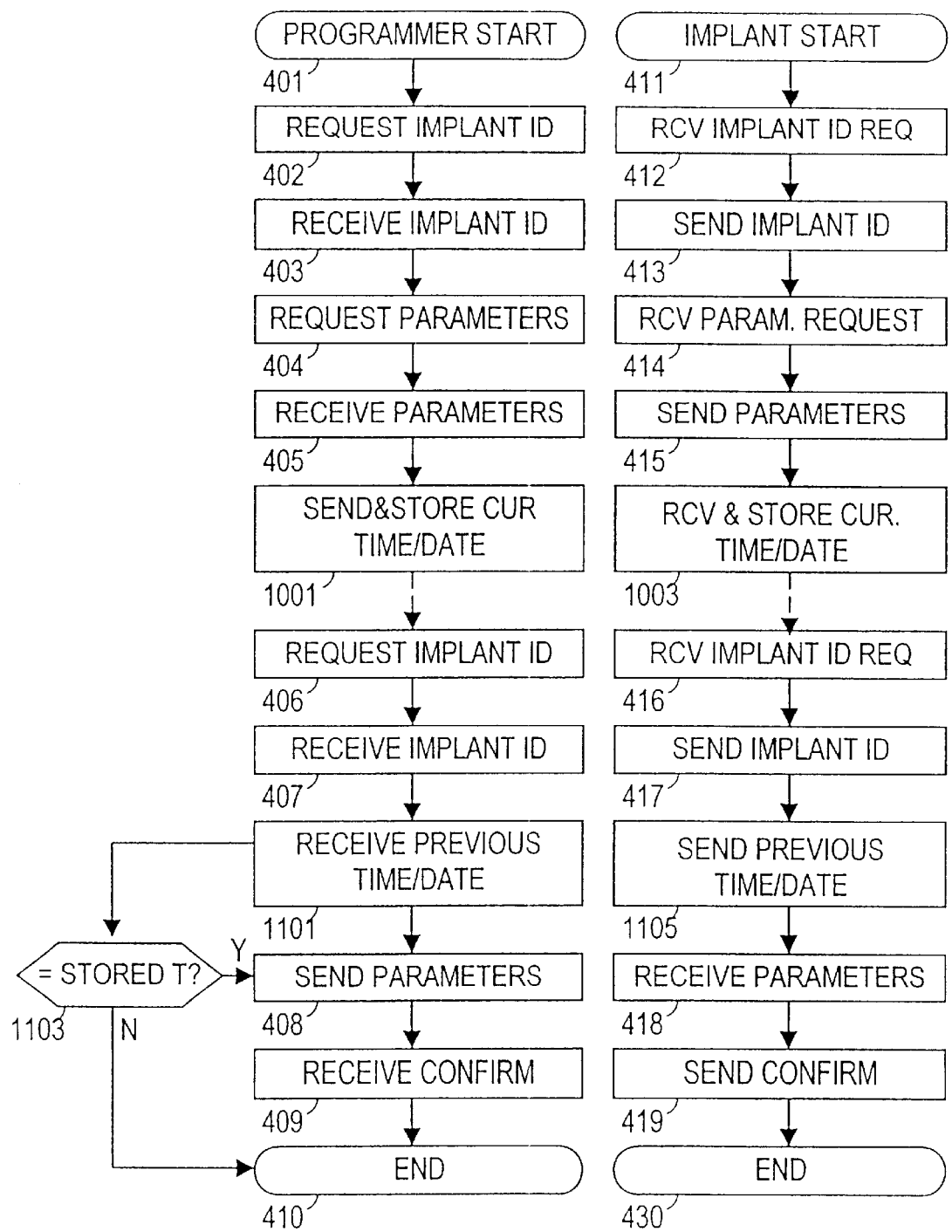
FIG. 11 is a flowchart depicting a sixth method for performing inquiry and programming operations in a multiprogrammer environment.

Two more system embodiments are shown in FIGS. 10 and 11. These embodiments are closely related to those of FIGS. 6 and 7, respectively. However, rather than using the programming device's identification number to identify the programming devices, these embodiments use the time and date of last access to identify the programming devices.

Referring now to FIG. 10, after the programming device's processor 302 successfully receives all the requested parameters in step 405, in step 1001 the processor 302 stores and sends a current time and date to the implantable device for the implantable device to keep on record. Subsequently, when the processor 302 is instructed to send altered parameters to the implantable device, the processor 302 performs steps 406, 407 and then in step 1002 transmits the stored time and date to the implantable device before proceeding with the remaining steps 408–410.

The implantable device's processor 204 performs steps 411–415 of the inquiry operation and in step 1003 receives and stores the date and time transmitted by the programming device. In the subsequent programming operation the processor 204 performs steps 416, 417 before receiving the transmitted time and date from the programming device in step 1004. Then in step 1006 the processor 204 compares the transmitted time and date to the stored time and date at which the last programming device successfully inquired or programmed the implantable device. If the numbers do not match, the processor 204 transmits a denial to the programming device in step 1008. Otherwise the processor 204 proceeds to receive the new parameters in step 418. Upon successful reception of all the transmitted parameters, the processor 204 sends a confirm signal in step 419 and stores the new parameters.

Referring now to FIG. 11, the inquiry operations of both the programming device and implantable device are the same as those of FIG. 10. In step 1105, the implantable device's processor 204 sends the stored date and time after establishing the implantable device's identity in steps 416–417, and before performing the remaining programming steps 418–420. After steps 406–407 of the programming operation, the programming device's processor 302 receives the date and time of last successful inquiry operation from the implantable device in step 1101. In step 1103, the processor 302 compares the received date and time to its own stored date and time of last successful operation to determine if any other programming device has successfully interacted with the implantable device since the current programming device's last inquiry operation. If the access date and times are the same, the processor 302 proceeds with steps 408–410 of the programming operation. Otherwise, the processor 302 terminates the program operation in step 410 and preferably notifies the user of the error.

Figure 12:
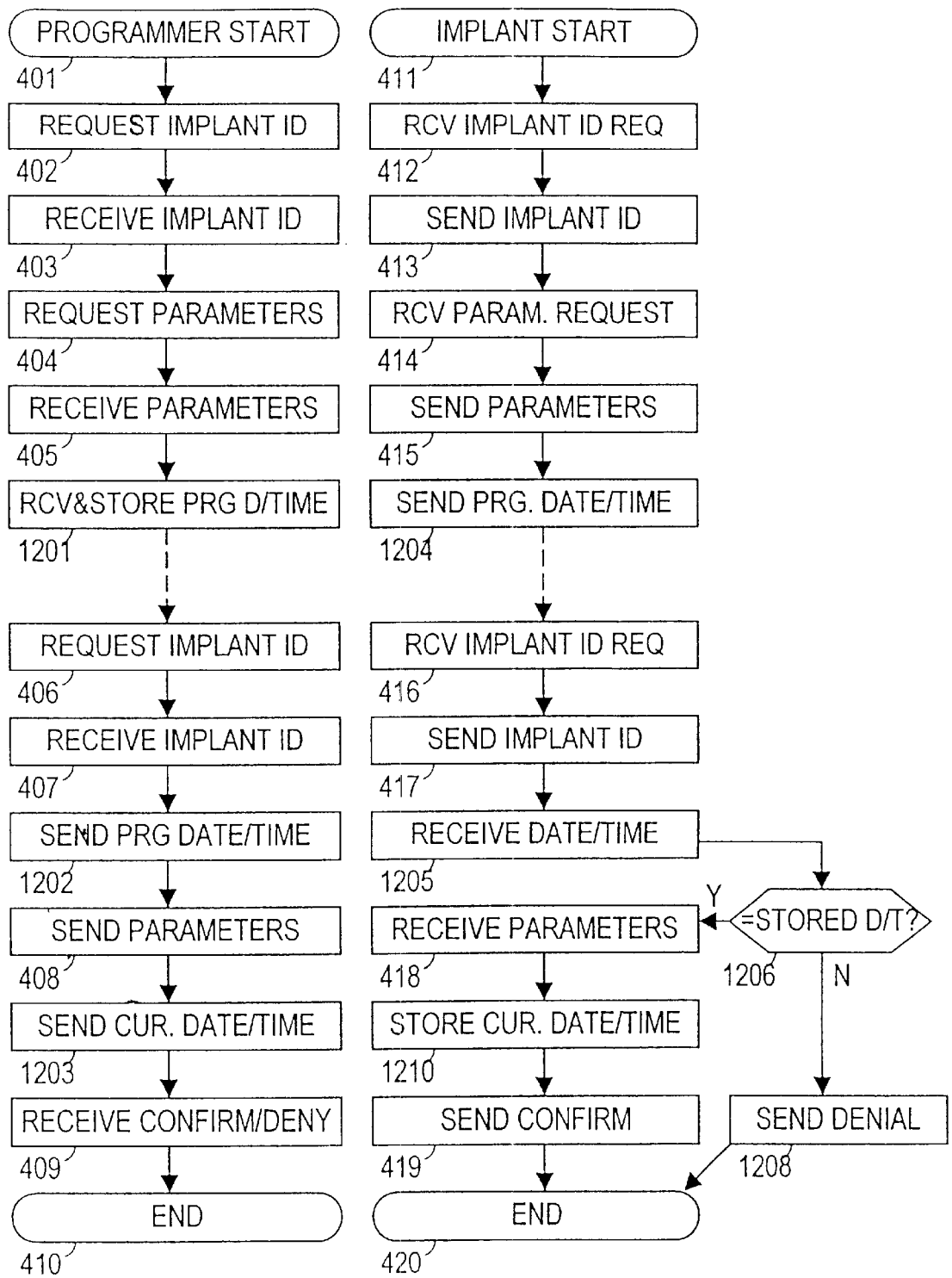
FIG. 12 is a flowchart depicting a seventh method for performing inquiry and programming operations in a multiprogrammer environment.

A preferred system embodiment is shown in FIG. 12. In this embodiment, a time and date is associated with the last successful programming of the implantable device 106. After the programming device's processor 302 performs steps 401–405 of the inquiry operation, in step 1201 it receives and stores the time and date of the last programming operation on the implantable device. In any subsequent programming operation, the processor 302 establishes the identity of the implantable device in steps 406–407 and sends the stored time and date in step 1202 before sending any parameters in step 408. After transmitting the parameters, the processor 302 sends the current date and time to the implantable device. The processor 302 then completes the programming operation steps 409–410.

After the implantable device's processor 204 performs inquiry operation steps 411–415, it sends the time and date of the last programming operation in step 1204. In the subsequent programming operation, the processor 204 establishes the implant's identity to the programming device in steps 416–417. In step 1205, the processor 204 receives the programming device's record of the last programming date and time, and compares it with the implantable device's record of the last programming date and time in step 1206. If they do not match, then the implantable device has been reprogrammed since the last inquiry operation by the programming device, and the processor 204 transmits a denial in step 1208 and terminates the programming operation in step 420. Otherwise, the processor 204 accepts the new parameters in step 418, and the current date and time in step 1210. If the programming operation is successful, the implantable device stores the current date and time as the new programming date and time, and in step 419 sends a confirmation to the programming device.

Figure 13:
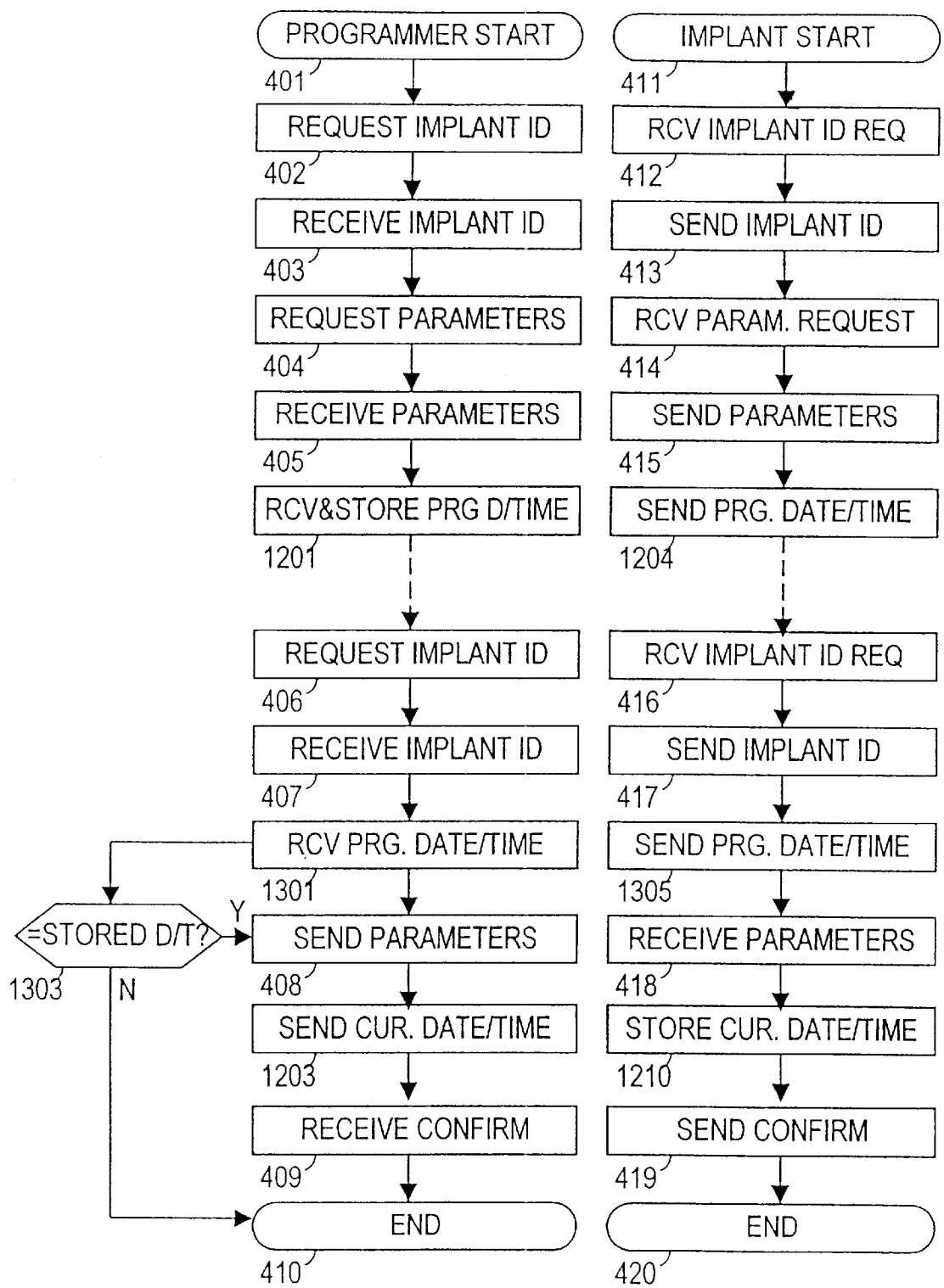
FIG. 13 is a flowchart depicting an eighth method for performing inquiry and programming operations in a multiprogrammer environment.

A more preferred embodiment is shown in FIG. 13. The inquiry operation is the same as the inquiry operation of the embodiment shown in FIG. 12. The programming operation differs for the implantable device in that after transmitting its identification information in step 417, the processor 204 transmits the stored programming date and time to the programming device in step 1305. The processor 204 then accepts any transmitted modified parameters in step 418 and if the transmission is successful, accepts and stores the current date and time in step 1210 before sending a confirmation in step 419.

The programming operation for the programming device begins with the processor 302 requesting and receiving the implantable device's identification information in steps 406–407. In step 1301 the processor receives the transmitted date and time from the implantable device and in step 1303 compares the transmitted date and time to the stored programming date and time. If they match, then none of the configuration parameters has been re-programmed since the programming device's last inquiry operation. Consequently, the processor 302 proceeds to send the new parameters in step 408 and the current date and time in step 1203. Otherwise, the programming device ends the program operation in step 410 and preferably notifies the operator of the error.

The embodiments of FIGS. 12 and 13 are preferred relative to the previously described embodiments since in these embodiments, multiple programming devices can simultaneously be qualified to provide a new set of parameters to the implantable device. Any programming device with a current version of the configuration parameters (as indicated by the associated programming date and time) can successfully program the implantable device. Conversely, in the other previously described embodiments, only a single programming device at a time (the one which has most recently interacted with the implantable device) can successfully program the implantable device.

Figure 14:
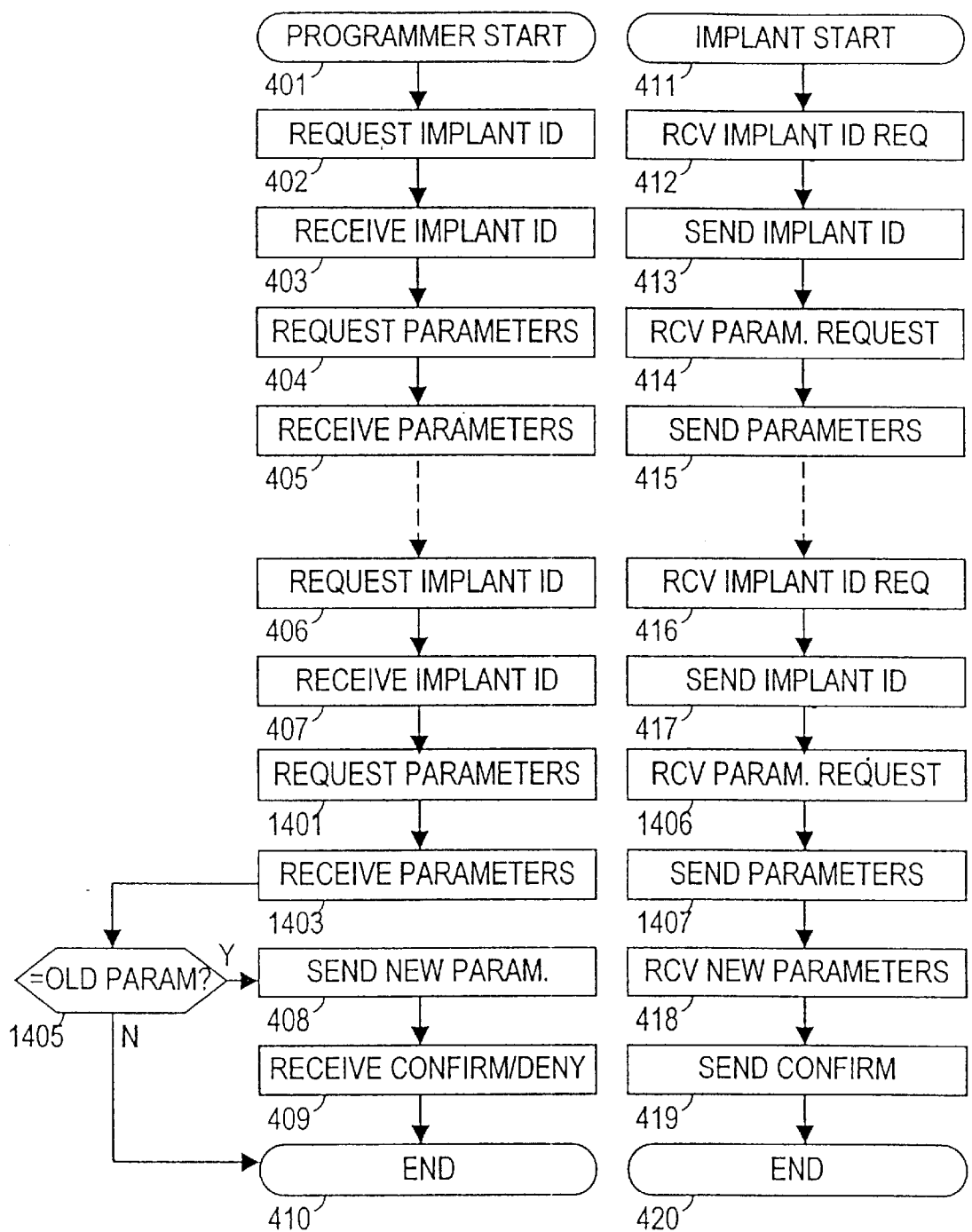
FIG. 14 is a flowchart depicting a ninth method for performing inquiry and programming operations in a multiprogrammer environment.

Referring now to FIG. 14, yet another embodiment is shown. In this embodiment, prior to each programming operation, programming device 110 inquires the configuration parameters in order to verify the accuracy of programming device 110's copy of those parameters. The inquiry operations for the implantable device and the programming device is the same as that of FIG. 4. For the programming operation, the implantable device's processor 204 performs steps 416–417 to establish its identity to the programming device. Then in step 1406 the processor 204 receives a parameter request similar to that of step 414, and in step 1407 responds to the parameter request by sending the requested parameters. Then in step 418 the processor 204 may receive modified parameters from the programming device, and in step 419 the processor 204 acknowledges a successful receipt of the parameters and updates the current parameters with the new parameter values.

The programming device's processor 302 performs steps 406–407 to establish the implantable device's identity, then in step 1401, the processor 302 transmits a request for the configuration parameters similar to that of step 404. The processor 302 receives the transmitted parameters in step 1403 and in step 1405 compares them with the parameters from the previous inquiry. If there is no change (or only a slight change which may be attributed to adaptation or progression of a programmed algorithm), then the implantable device has not been reprogrammed since the inquiry. The processor 302 consequently transmits the new configuration parameters in step 408. Otherwise, the programming device terminates the programming operation in step 410 and preferably notifies the user of the failure.

Numerous variations and modifications will become apparent to those skilled in the art once the above disclosure is fully appreciated. It is intended that the following claims be interpreted to embrace all such variations and modifications.

What is claimed is:

1. A multiprogrammer-aware implantable device which comprises:
   a memory configured to store configuration parameters;
   a telemetry module configured to transmit and receive external communications, said communications including configuration parameters; and
   a microprocessor coupled to the memory to read and write configuration parameters to said memory, and further coupled to the telemetry module to be adapted to send current configuration parameters to a programming device and to receive altered configuration parameters from the programming device, wherein the microprocessor is configured to perform an algorithm in a manner governed by the current configuration parameters, and
   wherein the microprocessor is configured to verify that the programming device has received the current version of the configuration parameters before accepting altered configuration parameters.

2. The implantable device of claim 1, wherein the memory stores an identification number, and wherein the microprocessor is configured to verify that the programming device has received a current version of the configuration parameters by receiving a programmer identification number from the programming device and compares the programmer identification number to the stored identification number which identifies a programming device that has made a most-recent inquiry of the implantable device.

3. The implantable device of claim 1, wherein the microprocessor is configured to verify that the programming device has received a current version of the configuration parameters by determining if a predetermined time interval has elapsed since a most recent inquiry of the implantable device.

4. The implantable device of claim 1, wherein the memory stores a time that indicates when a most-recent inquiry of the implantable device was made, and wherein the microprocessor is configured to verify that the programming device has received a current version of the configuration parameters by receiving an inquiry time from the programming device and comparing the inquiry time to the stored time.

5. The implantable device of claim 1, wherein the memory stores a time that indicates when a most-recent programming of the implantable device was performed, and wherein the microprocessor is configured to verify that the programming device has received a current version of the configuration parameters by receiving a programming time from the programming device and comparing the programming time to the stored time.

6. An implantable device, comprising:
   a memory configured to store configuration parameters;
   a telemetry module configured to transmit and receive external communications, said communications including configuration parameters; and
   a microprocessor coupled to the memory to read and write configuration parameters to said memory, and further coupled to the telemetry module to be configured to transmit current configuration parameters to a programming device and to receive altered configuration parameters from the programming device; and
   wherein the microprocessor is configured to verify that the programming device has received the current version of the configuration parameters before accepting altered configuration parameters.

7. The implantable device of claim 6, wherein the memory stores an identification number, and wherein the microprocessor is configured to verify that the programming device has received a current version of the configuration parameters by receiving a programmer identification number from the programming device and compares the programmer identification number to the stored identification number which identifies a programming device that has made a most-recent inquiry of the implantable device.

8. The implantable device of claim 7, wherein the microprocessor is configured to abort the communication of altered parameters from the programming device to the implantable device when the stored identification number and the programmer identification number do not match.

9. The implantable device of claim 8, further comprising a timer, and wherein the microprocessor is configured to send a request to the programming device to transmit configuration parameters, the microprocessor receives the configuration parameters and starts the timer after the configuration parameters are received, wherein the microprocessor determines when the timer has expired and transmits a denial to the programming device when the timer has expired and writes the altered parameters to the memory when the timer has not expired.

10. The implantable device of claim 6, wherein the memory stores a time that indicates when a most-recent inquiry of the implantable device was made, and wherein the microprocessor is configured to verify that the programming device has received a current version of the configuration parameters by receiving an inquiry time from the programming device and comparing the inquiry time to the stored time.

11. The implantable device of claim 6, wherein the memory stores a time that indicates when a most-recent programming of the implantable device was performed, and wherein the microprocessor is configured to verify that the programming device has received a current version of the configuration parameters by receiving a programming time from the programming device and comparing the programming time to the stored time.

* * * * *